US00PP24431P3

(12) United States Plant Patent
Deng et al.

(10) Patent No.: US PP24,431 P3
(45) Date of Patent: May 6, 2014

(54) ***CALADIUM* PLANT NAMED 'UF-18-49'**

(50) Latin Name: *Caladium hortulanum*
Varietal Denomination: UF-18-49

(75) Inventors: Zhanao Deng, Riverview, FL (US); Brent K. Harbaugh, Bradenton, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 53 days.

(21) Appl. No.: 13/508,000

(22) Filed: Aug. 10, 2012

(65) Prior Publication Data

US 2014/0047601 P1 Feb. 13, 2014

(51) Int. Cl.
*A01H 5/00* (2006.01)

(52) U.S. Cl.
USPC ..... Plt./373

(58) Field of Classification Search
USPC ..... Plt./373
See application file for complete search history.

(56) References Cited

PUBLICATIONS

U.S. Appl. No. 13/507,998, filed Aug. 10, 2013, Deng et al.
U.S. Appl. No. 13/507,999, filed Aug. 10, 2013, Deng et al.
Bell et al., "Survey of caladium tuber producers for acreage of cultivars grown," *Proc. Fla. State Hort. Soc.* 111:32-34, 1998.
Deng et al., "2003 survey of the Florida caladium tuber production industry," *Univ. Fla., Inst. Food Agric. Sci. EDIS Publication ENH 1007* <http://edis.ifas.ufl.edu/EP258>, 2005.
Geraldson et al., "Combination of high analysis fertilizers, plastic mulch and fumigation for tomato production on old agricultural land," *Proc. Soil and Crop Sci. Fla.* 25:18-24, 1965.
Harbaugh et al., "Commercial forcing of caladiums," IFAS, Univ. of Fla. Agr. Ext. Serv. Circ. 621, 13 pages, 1985.
Wilfret, "Florida Cardinal, caladium," *HortScience* 27(12):1342-1344,1992.

*Primary Examiner* — Kent L Bell
(74) *Attorney, Agent, or Firm* — Dentons US LLP

(57) ABSTRACT

A new and distinct cultivar of *Caladium* named 'UF-18-49' is disclosed. 'UF-18-49' is uniquely characterized with large fancy leaves, a large red center, strong vigor, excellent sunburn tolerance, and demonstrated potential to produce attractive plants when grown in containers or outdoor landscapes.

2 Drawing Sheets

ACKNOWLEDGEMENT OF FEDERAL RESEARCH SUPPORT

This invention was made with government support under FLA-BRA-04162 awarded by the Cooperative State Research, Education, and Extension Service, USDA. The government has certain rights in the invention.

Latin name of the genus and species of the plant claimed: *Caladium hortulanum.*

Variety denomination: 'UF-18-49'.

BACKGROUND OF THE INVENTION

*Caladiums [Caladium hortulanum* Birdsey, Araceae Juss.] are often used to provide color and a tropical ambiance to container gardening or the landscape. Red fancy-leaved cultivars represented 23% of the tuber producing industry in a 1998 survey (Bell et al., *Proc. Fla. State Hort. Soc.,* 111:32-34, 1998), compared to 29% and 28% for fancy white or pink cultivars, respectively. 'Frieda Hemple' (33%) and 'Postman Joyner' (13%) accounted for nearly half of the red cultivars grown. 'Florida Cardinal', released from a *Caladium* breeding program in 1988 (Wilfret, *Univ. Fla., Inst. Food Agric. Sci. Circ.*, S-351, 1988), comprised 7% of the red fancy-leaved cultivars grown, and was bred primarily for use in containers because it produces many leaves without the need to de-eye tubers.

The invention relates to a new and distinct cultivar of *Caladium hortulanum* plant named 'UF-18-49'. 'UF-18-49' originated from a planned cross between 'UF-702' (female parent, unpatented) and 'Red Flash' (male parent, unpatented). 'UF-702' was a breeding line derived from a cross between an unnamed sport of 'Aaron' and UF-FCB, a breeding line resulting from a cross between 'Fire Chief' and 'Buck'. 'Red Flash' and 'Aaron' are major commercial cultivars known for their attractive leaf colors, strong plant vigor, excellent sun tolerance, high tuber yields, and large tuber sizes (Bell et al., *Proc. Fla. State Hort. Soc.,* 111:32-34, 1998; Deng et al., *Univ. Fla., Inst. Food Agric. Sci., EDIS Publication #ENH*1007, Gainesville, Fla., 2008). 'Fire Chief' and 'Buck' are commercially produced on a much smaller scale, but they carry some unique characteristics: 'Fire Chief' produces red translucent leaves and 'Buck' produces deep, dark-red leaves. The ancestry of 'Aaron', 'Fire Chief', 'Red Flash', and 'Buck' is unknown. The cross that produced 'UF-18-49' was made in 2000. 'UF-18-49' was discovered and selected in 2001 within the progeny of the stated cross. Asexual propagation was performed by tubers and tuber division, and evaluation in field and pot studies in Bradenton, Fla. between 2001 and 2004 and in Wimauma, Fla. since 2005 have shown that the unique features of 'UF-18-49' are stable and true to type in successive generations of asexual propagation.

Plant Breeder's Rights for this cultivar have not been applied for. 'UF-18-49' has not been made publicly available more than one year prior to the filing of this application.

SUMMARY OF THE INVENTION

The new *Caladium* cultivar 'UF-18-49' has not been observed under all possible environmental conditions. Its phenotype may vary somewhat with variations in the environment, such as light intensity and temperature, without, however, any variance in genotype.

'UF-18-49' is uniquely characterized by large fancy leaves, a large red center, strong plant vigor, excellent sunburn tolerance, and the potential to produce attractive plants when tubers are forced in containers or planted in outdoor ground beds.

Compared to female parent 'UF-702' (unpatented), 'UF-18-49' plants are taller and more vigorous. In addition, leaves of 'UF-18-49' have a large red center, while leaves of 'UF-702' have a red rose face and red rose spots.

Compared to male parent 'Red Flash' (unpatented), 'UF-18-49' leaves are non-spotted, while leaves of 'Red Flash' have pink and white spots.

BRIEF DESCRIPTION OF THE DRAWINGS

The accompanying photographs illustrate the overall appearance of 'UF-18-49'. These photographs show the colors as true as it is reasonably possible to obtain in colored reproductions of this type. Colors in the photographs may differ slightly from the color values cited in the detailed botanical description, which accurately describe the colors of 'UF-18-49'.

DETAILED BOTANICAL DESCRIPTION

Figure 1:
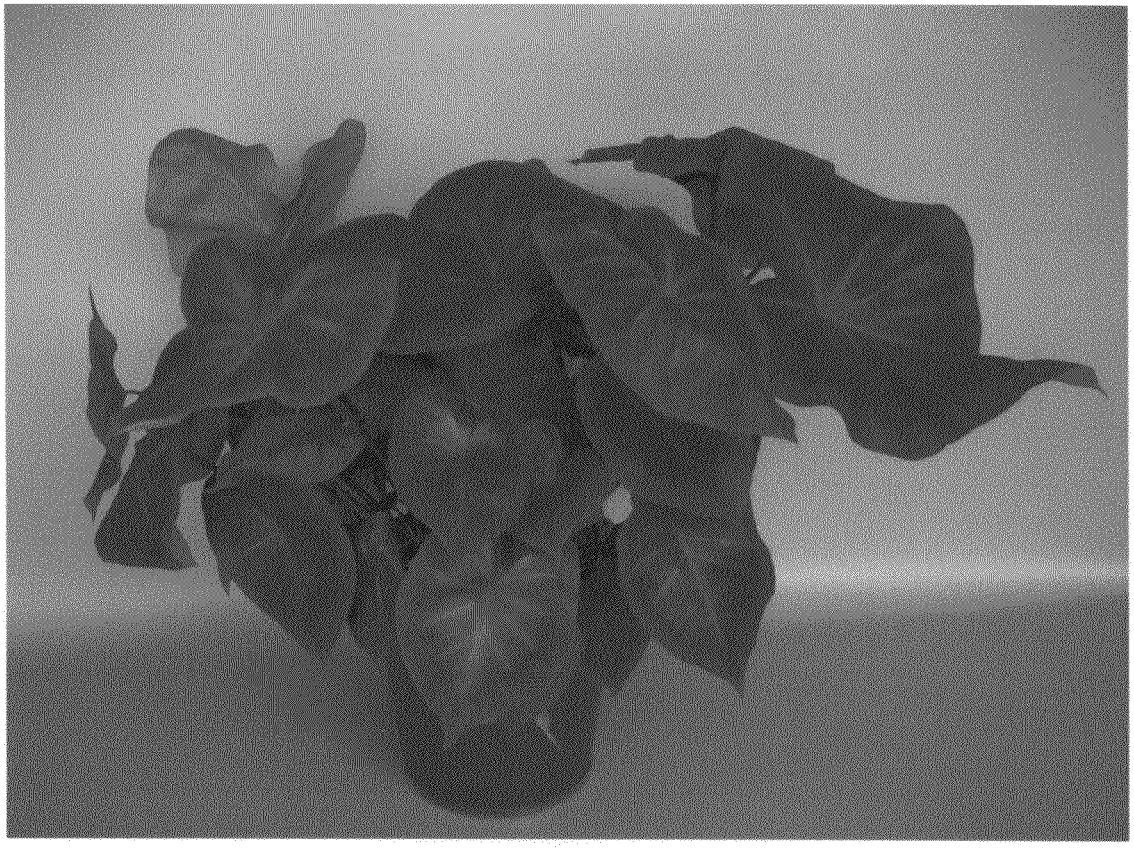
FIG. 1: Shows a side perspective view of a typical plant of 'UF-18-49' grown in a container in a shadehouse in Wimauma, Fla.
Figure 2:
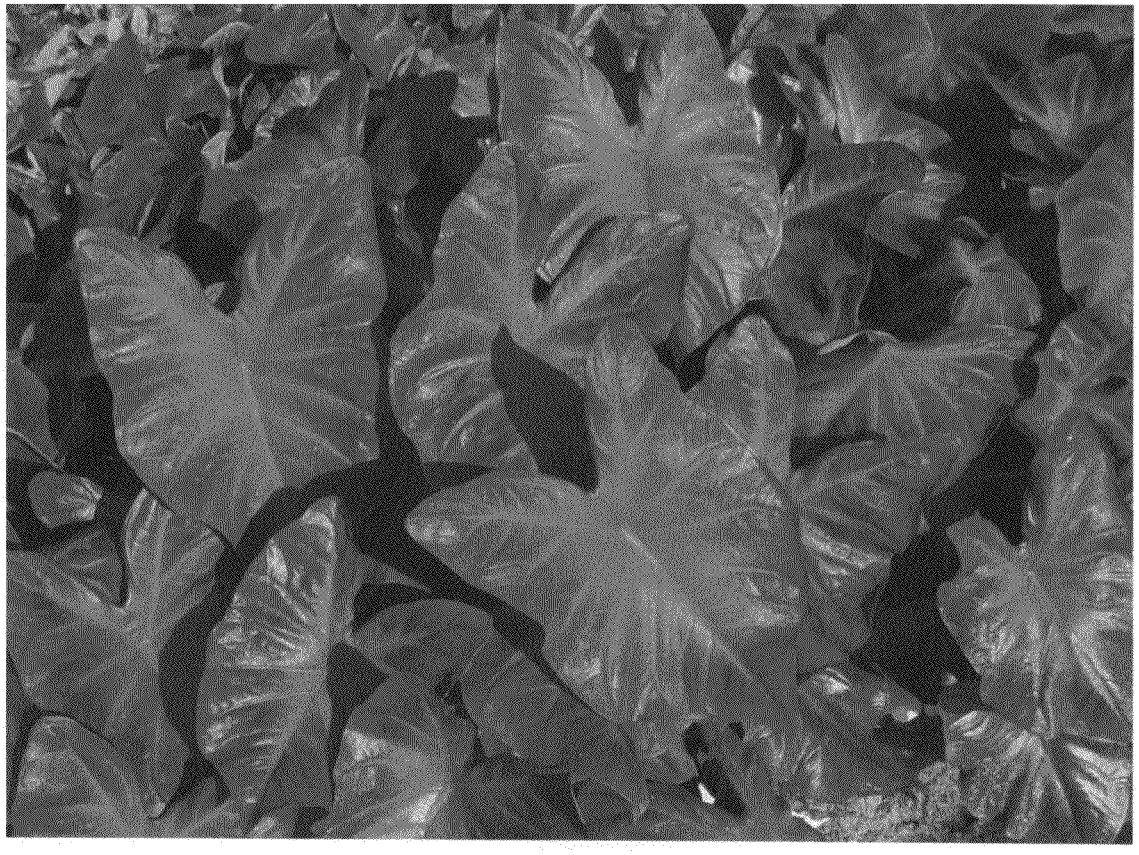
FIG. 2: Shows a side perspective view of typical plants of 'UF-18-49' grown in outdoor ground beds in full sun Wimauma, Fla.

In the following description, color references are made to The Royal Horticultural Society Colour Chart, 1986 Edition, except where general terms of ordinary dictionary significance are used.

The aforementioned photographs and following observations and measurements describe plants grown in 20.3-cm containers in Wimauma, Fla. during the summer in a polypropylene-covered shadehouse and plants grown in ground beds in Wimauma, Fla. during the late summer in an outdoor nursery. All plants were grown under conditions and practices which approximate those generally used in commercial *Caladium* production.

During the production of the plants, day temperatures ranged from about 23.5-34.4° C., night temperatures ranged from about 20.5-23.5° C. and light levels were about 944 (shadehouse) or 9744 foot-candles (outdoor nursery). Plants grown in the shadehouse were about eight weeks from planting tubers when the photographs and the detailed description were taken. Plants grown in the outdoor nursery were about fourteen weeks from planting tuber pieces when the photographs and the detailed description were taken.

Phenotypic description of *Caladium hortulanum* variety 'UF-18-49':

*Common name.*—*Caladium.*

Tuber description:

*Color.*—Epidermis: Brown (RHS 200C to 200D). Interior: Yellow (RHS) 10B.

Root description: Dense, thick and white fleshy roots.

Plant description:

*Plant type.*—Herbaceous perennial. Leaf petioles arising from tubers; petioles mostly upright and curving outwardly with development.

*Plant height, from soil level to top of leaf plane, shadehouse-grown plants.*—~22-23 cm.

*Plant height, from soil level to top of inflorescences, shadehouse-grown plants.*—No inflorescences observed on these plants.

*Plant diameter or spread, shadehouse-grown plants.*—~47 cm×42 cm.

*Plant height, from soil level to top of leaf plane, outdoor nursery-grown plants.*—~24-27 cm.

*Plant height, from soil level to top of inflorescences, outdoor nursery-grown plants.*—No inflorescences observed on plants grown in the outdoor nursery.

*Plant diameter or spread, outdoor nursery-grown plants.*—~47 cm×42 cm.

Foliage description (shadehouse-grown and outside grown):

*Length, shadehouse-grown plants.*—~17-19 cm.

*Width, shadehouse-grown plants (flattened).*—~12-14 cm.

*Length, outdoor nursery-grown plants.*—~17-22 cm.

*Width, outdoor nursery-grown plants (flattened).*—~12.5-17.5 cm.

*Shape.*—Peltate, ovate.

*Apex.*—Acuminate to acute.

*Base.*—Cordate.

*Margin.*—Entire.

*Texture, upper surface.*—Smooth, glabrous.

*Texture, lower surface.*—Smooth, glabrous, glaucous.

*Venation pattern.*—Palmate, pinnate.

*Color, shadehouse-grown plants.*—Developing and fully expanded leaves. Upper surface: Center: Greyed-purple (RHS 187B). Border and margins: Green (RHS 137A). Basal notch: Red (RHS 53B). Venation: Midrib and primary veins, all veins red (RHS 53B). Developing and fully expanded leaves. Lower surface: Center: Developing: greyed-green (RHS 191A); Expanded: Greyed-purple (RHS 187D). Border and margins: Greyed-green (RHS 191A). Venation: Midrib and primary veins, both are red-purple (RHS 60A to 60B) with some bleeding of greyed-purple (RHS 187D) around the veins.

*Color, outdoor nursery-grown plants.*—Developing leaves, upper surface: Center: Red (RHS 53C), darkening to red (RHS 53B) toward edges. Border and margins: Green (RHS 137A). Venation: Midrib and primary veins, both are greyed-purple (RHS 185A) with some netted veins red (RHS 53B). Developing leaves, lower surface: Center: Greyed-purple (RHS 185B). Border and margins: Yellow-green (RHS 147B). Venation: Midrib and primary veins, both are greyed-purple (RHS 182A), with bleeding of greyed-purple (RHS 185B) around primary veins. Fully expanded leaves, upper surface: Center: Greyed-purple (RHS 187B), darkening to greyed-purple (RHS 187A). Border and margins: Yellow-green (RHS 147A). Venation: Midrib and primary veins: Both red RHS (53A). Fully expanded leaves, lower surface: Center: Greyed-purple (RHS 185C). Border and margins: Yellow-green (RHS 147B). Venation: Midrib, greyed-red (RHS 181D) with small amounts of bleeding greyed-purple (RHS185C).

*Petiole.*—Aspect: Mostly erect, curving outwardly with development. Length, shadehouse-grown plants: ~21.5-23 cm. Diameter, distal, shadehouse-grown plants: ~3.5 mm. Diameter, proximal, shadehouse-grown plants: ~6.5 mm. Length, outdoor nursery-grown plants: ~21.5-26 cm. Diameter, distal, outdoor nursery-grown plants: ~3.6 mm. Diameter, proximal, outdoor nursery-grown plants: ~6.3 mm. Strength: Strong; flexible. Color, shadehouse-grown plants: Distal end: Greyed-purple (RHS 185B) or greyed-red (RHS 182D); Proximal end: Black (RHS 202A). Color, proximal, outdoor nursery-grown plants: Brown (RHS 200A) with occasional streaks of greyed-green (RHS 195B). Wing length, shadehouse-grown plants: ~3-4.5 cm. Wing diameter, shadehouse-grown plants: ~4.5-5 mm. Wing length, outdoor nursery-grown plants: ~5 cm. Wing diameter, outdoor nursery-grown plants: ~6.6 mm. Wing color, shadehouse-grown plants: Greyed-red (RHS 182C) with streaks of brown (RHS 200A) or black (RHS 202A). Wing color, outdoor nursery-grown plants: Brown (RHS 200A) with many streaks of greyed-green (RHS 196D).

Disease and insect resistance: Disease and insect resistance is typical of the species.

Performance:

'UF-18-49' was evaluated for tuber production and plant performance in Wimauma, Fla. in 2005 and 2006. The soil was an EauGallie fine sand with about 1% organic matter and a pH of 6.2. Plants were grown in a plastic-mulched raised-bed system maintaining a constant water table with seepage irrigation (Geraldson et. al., *Proc. Soil and Crop Sci. Soc. Fla.* 25:18-24, 1965). In 2005, ground beds were fumigated on February 25 (6 weeks before planting), with a mixture of 67% methyl bromide and 33% chloropicrin (by volume) at the rate of 392 $kg \cdot ha^{-1}$, and in 2006, the beds were fumigated on March 10, 10 days before planting, with the same fumigant mixture, but at the half rate (196 $kg \cdot ha^{-1}$). The beds were 91 cm wide and 20 cm high with *Caladium* seed pieces (cut tuber propagules, about 2.5 cm) planted 15 cm apart in 3 rows. Osmocote 18N-2.6P-10K 8-9 month controlled release fertilizer (Scotts Co., Marysville, Ohio) was applied to the bed surface when shoot tips were emerging from the soil with nitrogen at 336 $kg \cdot ha^{-1}$.

Field plots were organized in three randomized complete blocks, and each plot was 1.25 $m^2$ with 30 plants. In 2005, seed tuber pieces were planted in April, and tubers were harvested in November; in 2006, seed pieces were planted in April, and tubers were harvested in December. Dried tubers were graded by maximum diameter: No. 2 (2.5-3.8 cm), No. 1 (3.8-6.4 cm), Jumbo (6.4-8.9 cm), Mammoth (8.9-11.4 cm), and Super Mammoth (>11.4 cm). The production index, an indicator of economic value of the harvested tubers, was calculated as: N (No. 2)+2N (No. 1)+4N (Jumbo)+6N (Mammoth)+8N (Super Mammoth); where N=number of tubers in each grade. An analysis of variance was conducted using the GLM procedure in the SAS program (SAS Institute, 2003) to compare the performance of 'UF-18-49' to that of 'Florida Cardinal', 'Frieda Hemple', and 'Postman Joyner', red fancy-leaved commercial cultivars.

'UF-18-49' was significantly more productive than all the commercial cultivars in 2005: Its tuber weight was 18-56% greater, number of marketable tubers 27-40% more, and production index 25-77.8% higher than the other tested red cultivars (Table 1). In 2006, 'UF-18-49' was comparable to 'Florida Cardinal', 'Frieda Hemple', and 'Postman Joyner' in tuber weight, number of marketable tubers, and production index, except that the number of marketable tubers for 'UF-18-49' was smaller than that of 'Frieda Hemple'. The size distribution of tubers produced by 'UF-18-49' in the 2005 and 2006 growing seasons was similar: approximately 60% tubers in No. 1 and Jumbo and approximately 20% in Mammoth. This distribution was desirable for a cultivar to be marketed for large container and landscape use.

TABLE 1

Tuber weight, production index, number, and grade distribution of four *Caladium* cultivars (2005 and 2006). Values presented are means of three replications with 30 propagules planted in a plot.

| Cultivar | Tuber Weight (kg) | Tuber Production index[y] | Tuber Marketable (no.) | Tuber distribution[z] (%) Super mammoth | Tuber distribution[z] (%) Mammoth |
|---|---|---|---|---|---|
| | | Year 2005 | | | |
| 'UF-18-49' | 3.9 | 160 | 44.4 | 6.0 | 18.0 |
| 'Florida Cardinal' | 2.8 | 113 | 34.3 | 3.3 | 12.7 |
| 'Frieda Hemple' | 3.3 | 128 | 35.0 | 6.7 | 17.3 |
| 'Postman Joyner' | 2.5 | 90 | 31.7 | 0 | 10.0 |
| | | Year 2006 | | | |
| 'UF-18-49' | 4.4 | 134 | 39.7 | 3.3 | 17.7 |
| 'Florida Cardinal' | 4.1 | 137 | 35.2 | 6.3 | 26.7 |
| 'Frieda Hemple' | 5.2 | 159 | 48.8 | 6.0 | 17.3 |
| 'Postman Joyner' | 3.8 | 115 | 36.6 | 2.7 | 27.0 |

| Cultivar | Tuber distribution[z] (%) Jumbo | No. 1 | No. 2 |
|---|---|---|---|
| | Year 2005 | | |
| 'UF-18-49' | 32.7 | 30.7 | 12.7 |
| 'Florida Cardinal' | 40.0 | 30.0 | 14.7 |
| 'Frieda Hemple' | 38.0 | 28.0 | 9.3 |
| 'Postman Joyner' | 27.0 | 54.3 | 9.3 |
| | Year 2006 | | |
| 'UF-18-49' | 31.0 | 32.0 | 15.7 |
| 'Florida Cardinal' | 28.7 | 26.7 | 11.0 |
| 'Frieda Hemple' | 22.0 | 35.3 | 18.7 |
| 'Postman Joyner' | 13.0 | 42.7 | 18.7 |

[z]Tubers graded by maximum diameter; No. 2 (2.5-3.8 cm), No. 1 (3.8-6.4 cm), Jumbo (6.4-8.9 cm), Mammoth (8.9-11.4 cm), and Super Mammoth (>11.4 cm). Tuber distribution data (%) were transformed using the formula arcsine [square root (percentage/100)] before analysis of variance and mean separation.

[y]The production index is an indicator of economic value of the crop harvested and is calculated as: N (No. 2) + 2N (No. 1) + 4N (Jumbo) + 6N (Mammoth) + 8N (Super Mammoth), where N = number of tubers in each grade.

Landscape performance of cultivars grown under full-sun conditions was evaluated in 2005 and 2006 on the same plots used for evaluating tuber production. The overall plant performance was rated in two growing seasons, on a scale of 1 to 5, with 1 being very poor (few leaves and lack of vigor), and 5 being excellent (full plants, numerous leaves, and bright color display). Leaf sunburn tolerance was also evaluated in each growing season on a scale of 1 to 5, with 1 being very susceptible to sunburns and showing numerous sun-damaged areas or holes on leaves and 5 being resistant to sunburns and not showing any sun-damaged areas. Approximately 4 months after planting, plant height, number of leaves, and foliar characteristics were measured.

'UF-18-49' plants were 8-27 cm taller, and leaves were 5-27 cm longer and 3-7 cm wider than those of 'Florida Cardinal', 'Frieda Hemple', and 'Postman Joyner' (Table 2). Therefore, 'UF-18-47' produced the tallest plants with the largest leaves for this red fancy-leaved cultivar group. Sunburn tolerance ratings of 'UF-18-49' plants were between 3.9 and 4.6, significantly higher than the rating scores of 'Florida Cardinal' in all five evaluations (1.8-2.8), and higher than those of 'Postman Joyner' in four of five evaluations (2.5-3.9), and even higher than the scores of 'Frieda Hemple' (currently the most popular red cultivar being sold) in three out of five evaluations (2.7-4.0). With this sunburn tolerance and outstanding vigor, 'UF-18-49' plants received the highest landscape performance ratings, 4.0-4.8, which were much higher than those of 'Florida Cardinal' and 'Postman Joyner' (1.7-2.9). The ratings of 'UF-18-49' were also significantly higher than the ratings of 'Frieda Hemple' in two of five evaluations.

TABLE 2

Plant characteristics, performance and sun tolerance from planting 2.54-cm *Caladium* tuber propagules in ground beds in full sun (2005 and 2006). Values presented for plant height, leaf number, length, and width are means of three replications with three plants measured per plot per year, while performance and sunburn tolerance ratings are means of three replications based on whole plot evaluation.

| | Plant height[z] | Leaf number[z] | length[z] | width[z] | Performance rating[y] 2005 | | |
|---|---|---|---|---|---|---|---|
| Cultivar | (cm) | (no.) | (cm) | (cm) | June | July | August |
| 'UF-18-49' | 51.3 | 19.9 | 32.3 | 21.2 | 4.0 | 4.8 | 4.8 |
| 'Florida Cardinal' | 24.6 | 19.3 | 21.6 | 14.4 | 1.7 | 2.3 | 2.9 |
| 'Frieda Hemple' | 43.5 | 23.4 | 26.3 | 17.7 | 3.3 | 4.5 | 4.2 |
| 'Postman Joyner' | 35.7 | 13.4 | 26.8 | 16.4 | 1.6 | 2.0 | 2.8 |

| | Performance rating[y] | | Sun tolerance rating[z] | | | | |
|---|---|---|---|---|---|---|---|
| | 2006 | | 2005 | | | 2006 | |
| Cultivar | August | September | June | July | August | August | September |
| 'UF-18-49' | 4.3 | 4.5 | 2.6 | 3.9 | 4.6 | 4.0 | 4.3 |
| 'Florida Cardinal' | 1.5 | 2.4 | 1.8 | 2.1 | 2.7 | 2.0 | 2.8 |
| 'Frieda Hemple' | 4.2 | 4.4 | 2.7 | 4.0 | 3.6 | 3.8 | 3.9 |
| 'Postman Joyner' | 2.2 | 2.6 | 3.9 | 2.5 | 3.8 | 2.3 | 3.5 |

[z]Data were taken over two growing seasons (2005 and 2006), approximately 4 months (August 2005 and 2006) after tubers were planted in April each year.
[y]Plants were rated on a scale of 1 to 5, with 1 being very poor, 3 being fair and acceptable, and 5 being excellent in plant vigor, fullness, and color display, in July, August, and September of 2005, and August and September of 2006, respectively.
[x]Plant sunburn tolerance was rated on a scale of 1 to 5, with 1 being very poor, 3 being fair and acceptable, and 5 being excellent without showing any signs of leaf burns or resulted holes on leaf surfaces, taken in July, August, and September of 2005 and August and September of 2006, respectively.

The suitability for container forcing was evaluated by forcing tubers in 11.4-cm containers. No. 1 tubers were planted either intact or de-eyed in a peat/vermiculite mix (VerGro Container Mix A, Verlite, Tampa, Fla.) on Mar. 26, 2007. The study was conducted in a greenhouse with 45% light exclusion during the summer in Wimauma, Fla. Average daily temperatures ranged from a low of 16° C. at night to 29° C. during the day throughout the experiment. Potted plants were arranged on metal benches in the greenhouse in a randomized complete block design with 10 replications. Plant height, number of leaves, and foliar characteristics were recorded 8 to 10 weeks after planting.

'UF-18-49' sprouted approximately 30 days after planting either intact or de-eyed tubers, and was similar to 'Florida Cardinal' in sprouting time in container forcing, but approximately 5 days later than 'Frieda Hemple' and approximately 2-4 days later than 'Postman Joyner' (Table 3). When tubers were planted intact, forced 'UF-18-49' plants were the tallest with a height of 40.5 cm, 7-10 cm taller than plants of 'Frieda Hemple' and 'Postman Joyner'. When tubers were de-eyed before planting, no significant differences in height were observed between 'UF-18-49', 'Frieda Hemple', and 'Postman Joyner'. Leaves of 'UF-18-49' were again longer (3-5 cm) and wider (3-5 cm) than the leaves of the other cultivars, whether or not tubers were de-eyed. 'UF-18-49' was similar to 'Postman Joyner' in leaf development, producing 8-10 leaves within 8 weeks after planting. Both of these cultivars produced fewer leaves than 'Florida Cardinal' and 'Frieda Hemple'. Pot plant quality rating of 'UF-18-49' was greater than 4.0, higher than that of 'Florida Cardinal' and 'Postman Joyner' and similar to that of 'Frieda Hemple'.

TABLE 3

Plant performance for *Caladium* cultivars grown from No. 1 tubers in 11.4-cm containers in a 45% shaded glasshouse, Wimauma, Florida. Values represent the means of 10 plants produced from intact or de-eyed No. 1 (3.8-6.4 cm in diameter) tubers planted individually per container. Data were taken 8 weeks after planting.

| | Days to sprout[z] | | Plant height (cm) | | Leaves (no.) | |
|---|---|---|---|---|---|---|
| Cultivar | Intact | De-eye | Intact | De-eye | Intact | De-eye |
| 'UF-18-49' | 30.3 | 29.8 | 40.5 | 37.9 | 9.0 | 9.9 |
| 'Florida Cardinal' | 28.3 | 32.9 | 33.0 | 28.4 | 13.1 | 17.0 |
| 'Frieda Hemple' | 24.6 | 25.1 | 29.8 | 34.9 | 16.3 | 21.0 |
| 'Postman Joyner' | 25.9 | 27.6 | 33.1 | 36.1 | 8.1 | 9.4 |

| | Leaf length (cm) | | Leaf width (cm) | | Quality rating | |
|---|---|---|---|---|---|---|
| Cultivar | Intact | De-eye | Intact | De-eye | Intact | De-eye |
| 'UF-18-49' | 28.0 | 22.6 | 20.4 | 16.4 | 3.9 | 4.2 |
| 'Florida Cardinal' | 23.6 | 17.8 | 16.8 | 11.8 | 2.5 | 3.3 |
| 'Frieda Hemple' | 23.3 | 17.8 | 17.1 | 12.1 | 3.8 | 4.1 |
| 'Postman Joyner' | 24.5 | 19.0 | 17.1 | 13.1 | 2.5 | 3.5 |

[z]Number of days from planting to the first unfurled leaf.

What is claimed is:

1. A new and distinct cultivar of *Caladium* plant named 'UF-18-49' as illustrated and described herein.

* * * * *